US009707554B2

(12) United States Patent
Broyer et al.

(10) Patent No.: US 9,707,554 B2
(45) Date of Patent: Jul. 18, 2017

(54) SIMPLIFIED DEVICE FOR NUCLEIC ACID AMPLIFICATION AND METHOD FOR USING SAME

(75) Inventors: Patrick Broyer, St Cassien (FR); Laurent Drazek, Grenoble (FR); Agnès Dupont Filliard, Les Adrets (FR); Michel Guy, Grenoble (FR); Frédéric Pinston, Grenoble (FR); Magaly Ponsard-Fillette, Grenoble (FR); Thierry Kollaroczy, Engins (FR)

(73) Assignee: bioMérieux, S.A., Marcy l'Etoile (FR)

( * ) Notice: Subject to any disclaimer, the term of this patent is extended or adjusted under 35 U.S.C. 154(b) by 637 days.

(21) Appl. No.: 13/395,348

(22) PCT Filed: Sep. 17, 2010

(86) PCT No.: PCT/FR2010/051936

§ 371 (c)(1), (2), (4) Date: Mar. 9, 2012

(87) PCT Pub. No.: WO2011/033231

PCT Pub. Date: Mar. 24, 2011

(65) Prior Publication Data

US 2012/0171662 A1 Jul. 5, 2012

(30) Foreign Application Priority Data

Sep. 18, 2009 (FR) ..................................... 09 04469

(51) Int. Cl.
*C12Q 1/68* (2006.01)
*B01L 3/02* (2006.01)
(Continued)

(52) U.S. Cl.
CPC ........... *B01L 3/0217* (2013.01); *B01L 3/5027* (2013.01); *B01L 7/52* (2013.01);
(Continued)

(58) Field of Classification Search
None
See application file for complete search history.

(56) References Cited

U.S. PATENT DOCUMENTS

| | | | | |
|---|---|---|---|---|
| 4,756,884 | A | 7/1988 | Hillman et al. | |
| 6,767,733 | B1 * | 7/2004 | Green | 435/288.5 |

(Continued)

FOREIGN PATENT DOCUMENTS

| | | |
|---|---|---|
| EP | 0212314 | 3/1987 |
| EP | 0674009 | 9/1995 |

(Continued)

OTHER PUBLICATIONS

Translation for the Written Opinion of the International Searching Authority for PCT/FR2010/051936.

(Continued)

*Primary Examiner* — Betty Forman

(57) ABSTRACT

The present invention relates to a disposable device (100) for amplifying at least one target nucleic acid present in a liquid and biological sample of interest, which consists of a solid body (2), at least one fluid channel (3) connecting an inlet (4), via which all or part of the sample of interest can be drawn up and/or discharged, and an outlet (5), which is itself connected to a means for the drawing up/discharging of the said sample of interest, the fluid channel (3) further comprising from the inlet (4) to the outlet (5):

- a first compartment (8) containing all or part of the thermostable constituents,
- a means (15) for mixing the constituents with the sample of interest,
- a second compartment (9) containing all or part of the non-thermostable constituents,
- and in addition, at least one zone intended for heating the said sample of interest (6) mixed with the said amplification constituents in order to allow the amplification of the target nucleic acid.

(Continued)

The invention also proposes an amplification method using such a device.
The said invention has a preferred application in the field of medical diagnosis.

11 Claims, 8 Drawing Sheets

(51) Int. Cl.
*B01L 3/00* (2006.01)
*B01L 7/00* (2006.01)

(52) U.S. Cl.
CPC ... *B01L 2200/0621* (2013.01); *B01L 2200/16* (2013.01); *B01L 2300/0864* (2013.01); *B01L 2400/0478* (2013.01); *B01L 2400/086* (2013.01)

(56) References Cited

U.S. PATENT DOCUMENTS

| | | | | |
|---|---|---|---|---|
| 7,059,351 | B1 | 6/2006 | Chu et al. | |
| 2003/0148922 | A1* | 8/2003 | Knapp et al. | 514/1 |
| 2005/0089863 | A1* | 4/2005 | Karlsen et al. | 435/6 |
| 2007/0026421 | A1* | 2/2007 | Sundberg | B01L 3/5027 435/6.12 |

FOREIGN PATENT DOCUMENTS

| | | |
|---|---|---|
| EP | 0733714 | 9/1996 |
| EP | 1187678 | 3/2002 |
| EP | 1715341 | 10/2006 |
| JP | S62-129759 A | 6/1987 |
| JP | 2003-522963 | 8/2001 |
| WO | 99/33559 | 7/1999 |
| WO | 01/61041 | 8/2001 |
| WO | 2004/004904 | 1/2004 |
| WO | 2004/045754 | 6/2004 |
| WO | 2006/122310 | 11/2006 |
| WO | 2006/132886 | 12/2006 |
| WO | 2007/002588 | 1/2007 |
| WO | 2007/100500 | 9/2007 |
| WO | 2008/006502 | 1/2008 |

OTHER PUBLICATIONS

Didenko, V.V., Fluorescent Energy Transfer Nucleic Acid Probes in Methods in Molecular Biology, 2006, p. 4, Humana Press.
Egholm et al.; Peptide Nucleic Acids (PNA). Oligonucleotide Analogues with an Archiral Peptide Backbone. J. Am. Chem. Soc., 1992, v.114, 1895-1897.
Seitz; Chemically Modified Antisense Oligonucleotides—Recent Improvements of RNA Binding and Ribonuclease H Recruitment. Chem. Int. Ed. 1992, v.38, No. 23, 3466-3469.
Sun et al.; Sequence and pH Effects of LNA-Containing Triple Helix-Forming Oligonucleotides; Physical Chemistry, Biochemistry, and Modeling Studies, Biochemistry, 2004, v.43, No. 14, 4160-4169.
English Translation of Notice of Reasons for Rejection, Japan Patent Office, dated Oct. 28, 2014 in Japanese Patent Application No. 2012-529330.

* cited by examiner

Coupe A - A

SIMPLIFIED DEVICE FOR NUCLEIC ACID AMPLIFICATION AND METHOD FOR USING SAME

CROSS REFERENCE TO RELATED APPLICATIONS

This application is the national stage application under 35 USC §371 of International Application No. PCT/FR2010/051936, filed Sep. 17, 2010, which claims the benefit of French Patent Application No. 0904469, filed Sep. 18, 2009, the disclosures of which are hereby incorporated by reference.

The present invention relates to a disposable device for amplifying at least one target nucleic acid. The present invention also relates to a method for amplifying such a target nucleic acid, using an abovementioned device. The device, like the method, can be used with any type of amplification technique, such as PCR, or a post-transcriptional amplification technique, such as TMA or NASBA.

The prior art is represented by document WO-A-99/33559 which relates to a built-in reaction cartridge for handling fluids, but also to document WO-A-2006/132886, from the same applicant, which relates to a method and an apparatus for storing and using reagent beads. This system comprises a compact instrument having four identical and demountable modules, and a cartridge having a plurality of wells, which incorporates a multichannel valve. A piston serves to move the liquids from one well to another of the cartridge in order to mix them. Among the various zones of the cartridge, each is suitable either for:

- filtration on silica matrix to obtain a capture, a purification and a concentration of the sample analysed,
- lysis which, by means of glass beads and under the action of ultrasound generated by an instrument, serves to lyse the cell membranes of the cells present in the sample,
- amplification which is carried out by transfer of all or part of the eluate into the amplification and detection zone (PCR) of the cartridge. The cartridge may include solid or liquid reagents or both simultaneously.

This system is therefore fully built in and automated, with a fairly short result return time (about one hour).

However, owing to the concept selected, the cartridge is relatively complex and costly. It is therefore unsuitable for a high-sample-rate system. Moreover, it is not suitable for performing several tests per sample except by multiplexing the amplification primers and/or detection probes in the same volume. This makes the development of biological tests much more complex and time-consuming, with inevitable compromises in terms of detection performance.

Our invention is far more suitable for high rates because the card that we protect can be easily handled by a robot, like a simple pipetting cone.

Moreover, its lateral size is reduced, allowing the feasibility of a high rate architecture using a fluorescence reading carousel having an acceptable diameter for a system designed for a high sample rate. Finally, the elongated design, with a plane surface, makes it easy to move the card within a reading carousel which requires:

- ensuring good thermal contact for the thermal cycles (PCR type) or a constant and uniform temperature (NASBA, TMA type) while allowing the movement of the said card by sliding on the incubation blocks, and
- making a fluorescent reading, the card being easily movable in front of the various read heads (various wavelengths).

High sample rate means a rate higher than 300 tests per day, with a low cost per test and reduced size.

In comparison with this system, the present invention helps to obtain costs per test that are compatible with routine viral or microbiological diagnosis, at high sample rate, but also for portable tests for patients, also called POCT (Point of Care Testing), thanks in particular to the simplicity of the consumable developed, to its built-in pipetting function, and to the smaller amplification reaction volume, which helps reduce the cost per test (enzymes in molecular biology constitute the main portion of this cost per test for the "reagents" part and a decrease in reaction volume therefore helps to obtain a reduction proportional to the reduction in volume) (5 μL instead of 50 to 80 μL in these applications).

The prior art also includes document WO-A-2004/004904 which relates to an apparatus designed to perform rapid self-contained and mobile tests, in the particular context of bio-terrorism, biological warfare and POCT, the apparatus requiring a minimum of manual operations. This system uses a cartridge provided with inlet ports connected to a flexible bag having one or more compartments in which the amplification reagents (PCR) are freeze-dried. The fluorescence is read directly through the deformable flexible film. The bags are kept under vacuum, thereby making it possible, after the introduction of the nucleic acid samples via the consumable inlet port, to carry out an automatic and calibrated filling and to dissolve the freeze-dried reagents prior to the PCR amplification.

This device is unsuitable for performing routine tests at a high sample rate. This vacuum fluid distribution and/or division system is effective for one-step fluid protocols (filling) usable in the case of a PCR amplification. However, it is unsuitable for the method for amplifying nucleic acids, which require placing a plurality of reagents in suspension consecutively, as in the case for NASBA or TMA amplifications. This therefore requires adding a valve and maintaining a partial vacuum between the two chambers containing the amplification reagents, causing a complexification of the consumable and of the associated instrument. Moreover, the consumable is not suitable for directly drawing up the sample containing the nucleic acids (deposition by pipette) without manual action; hence there is no pipetting function. Furthermore, this device, which combines a rigid portion with a flexible bag portion, is not easily manageable in an architecture in which the user can place a sample at any time, even during the operation of the instrument, called a Random Access architecture.

Our invention, on the contrary, proposes a card which can easily be handled by a robot and can be used as a cone to pipette solutions, mix them, take up the eluate and draw it up to conduct reactions such as amplification reactions. The card, according to the present invention, can therefore be used as a pipette cone for making additions, drawing up liquid reagents into tubes, and thereby carrying out the steps prior to the amplification/detection step. With suitable automation, the said card can also sample and withdraw a plurality of cones simultaneously. For this purpose, embodiments comprising more than one fluid channel are presented in the rest of this document.

The present invention of the Applicant, by its original design, serves to adapt both to the PCR (or RT-PCR) amplification protocol only requiring one reagent (and therefore feasible in a single chamber) and the two-step amplification protocol requiring separation of the amplification reagents in two distinct chambers, as in the case of post-transcriptional amplifications. The invention also solves the problem of instrument architecture, by proposing a consumable (or card) usable either in the POCT system (a few tests per day) or in a routine high-rate diagnosis system (more than 300 tests per day) by integrating the pipetting function, which uses conventional cones (added on or built in).

The prior art also includes document WO-A-2007/100500. This concerns a highly oriented POCT system or the low rate in molecular biology. This easy-to-use system makes it possible to work directly from a drop of blood (a few tens of μL). The associated instrument is also compact thanks to a combination of actuators designed to isolate the compartments of the tubular consumable and thereby allow the transfer and mixing of the liquids in the order defined in manufacture by the prior filling of the consumable.

A major drawback of this system is its lack of flexibility for the biological protocol to be followed. On the one hand, the sample and buffer volumes (magnetic nucleic acid capture particles, washing and elution buffers) are fixed by the volume of each compartment of the consumable, as defined during the manufacture of the consumable. It is known that it is often necessary to modify the biological protocol, in order to obtain better nucleic acid capture, amplification and detection performance according to various parameters, such as, for example, the type of biological sample treated, the presence or absence of inhibitors (spit, LBA, plasma, urine, whole blood, etc.). With this prior art system, modifying the protocols requires creating a different consumable every time with different volumes for each compartment, and thereby modifying the sealing zones, with a very strong limitation associated with the location of the zones where the mobile actuators are installed in the associated instrument (valves and pistons for the rupture of the said sealing zones by overpressure). Furthermore, the sample volume remains very small and therefore does not cover all the needs of the users, particularly in tests with several milliliters of sample. Moreover, the flexible object is difficult to manage by a robot except at high extra cost. It has no pipetting function, nor flexibility in the choice of the elution and washing volumes, and therefore has less flexibility in sample preparation.

The applicant has also filed a number of documents which can constitute the prior art. These concern in particular patent application EP-B-1.187.678 which relates to a device for using an analysis card in which fluid reaction and transfer steps are carried out under the action of control means built into the card.

One problem of this type of device is that it is forced to operate with the help of valves which consist of elements that are deformable under the action of an actuator, thereby causing the direct or indirect closure of the channels associated with the valves. The essential problem with this device is its complexity. Thus, the presence of valves considerably complicates the manufacture of the analysis card thus formed and adds to its production cost, and furthermore, many external elements (actuators) are needed to actuate all the said valves.

The present invention proposes to solve the problems highlighted by all the abovementioned prior art documents. For this purpose, it proposes a device which is disposable and which satisfies a number of technical characteristics.

In a particularly advantageous embodiment of the invention, the device is a consumable which is considered like a pipette, carrying the dried or freeze-dried reagents required for an amplification of RNA or DNA targets from a reduced volume of nucleic acids (5 to 10 μL), thereby cutting the costs linked to the reagents, and incorporating a valve to eliminate any risk of contamination. This is a slide valve, normally open and then closed after locating the reaction volume in the reading zone, when there are no further steps to be carried out. This type of device has many features unknown in the prior art:

- Based on this concept, the ability to manufacture robots in a POCT version (processing by batch of 8-24 samples per batch) and in a high-rate robot version using the same consumable.
- Automatic sampling, by moving the tip that is added on or is an integral part of the inventive device, of the volume of purified nucleic acid serving to reduce the number of manual steps, thereby consequently serving to simplify the automation of a robot apparatus using such consumables.
- Ability to incorporate, in a single associated instrument, a PCR or NASBA amplification for POCT.
- Simplification of the instrumentation by the inclusion in the device of carried and freeze-dried or dried reagents, which can be dissolved and mixed consecutively by simple movement within the said device, the configuration of the fluid circuit of which facilitates this dissolution and this mixing.
- Ability to perform mono-tests (one set of amplification primers per fluid channel within the device), multiplex tests (with at least two sets of primers per channel) or by panel (at least two separate sets of primers in at least two channels) from a common instrumental architecture.
- Total automation of the amplification protocol with an inexpensive device and compact associated instrumentation.
- Shorter total amplification time (especially with NASBA) by reducing the denaturation time in comparison with a "conventional" amplification (1 minute versus 5 to 10 minutes) due to the heating through the thin cover film of the reaction channel, instead of a thicker plastic tube, whose thermal inertia is unfavourable.
- No lifetime limitation of the enzyme compared to conventional automation, because the reagents, carried in the said device, remain dry until being taken up by the liquid sample to be amplified.

The present invention relates to a disposable device for amplifying at least one target nucleic acid present in a liquid and biological sample of interest, which consists of a solid body, at least one fluid channel connecting an inlet, via which all or part of the sample of interest can be drawn up and/or discharged, and an outlet, which is itself connected to a means for the drawing up/discharging of the said sample of interest, the fluid channel further comprising from the inlet to the outlet:

- a first compartment containing all or part of the thermostable constituents required for producing the amplification,
- a means for mixing the constituents with the sample of interest,
- a second compartment containing all or part of the non-thermostable constituents required for producing the amplification,
- and in addition, at least one zone intended for heating the said sample of interest mixed with the said amplification constituents, in order to allow the amplification of the target nucleic acid.

According to an embodiment, the device for detecting amplicons is characterised in that it further comprises, in the second compartment, all or part of the detection constituents required for detecting the amplicons.

According to another embodiment, the device for detecting amplicons is characterised in that it further comprises, in the fluid channel, a third compartment containing all or part of the constituents required for detecting the amplicons.

Also in another embodiment, the device further comprises, in the fluid channel, a third compartment containing nothing but serving for the subsequent detection of the amplicons in a clean environment.

In an alternative embodiment of the device, described in the previous paragraph, the third compartment is located between the second compartment and the outlet of the device.

Regardless of the alternative embodiment, the inlet of the device accommodates a cone of a pipette or the tip of the pipette has a pipette-cone-shaped configuration.

Regardless of the preceding alternative embodiment, the drawing up/discharging device is of the piston type such as, for example, a pipette.

Regardless of the preceding alternative embodiment, the cross-section of the channel is constant and the compartments have a larger cross-section.

According to a multichannel embodiment, the inlet communicates with at least two fluid channels.

Also according to a multichannel embodiment, the outlet comprises at least two fluid channels.

Regardless of the preceding alternative embodiment, the constituents are formed of freeze-dried or dried biological compounds, soluble in the sample of interest.

Regardless of the preceding alternative embodiment, the drawing up/discharging means is an integral part of the disposable device.

According to the latter alternative embodiment, the drawing up/discharging means comprises a cylinder connected to the fluid channel and a piston moving within the cylinder manually or by means of an actuator.

Regardless of the preceding alternative embodiment, the mixing means consists of the fluid channel, the routing of which comprises at least one baffle.

The present invention also proposes a method for amplifying at least one target nucleic acid, present in a liquid and biological sample of interest, made within a device previously described, which consists in:

(a) drawing up via the inlet all or part of the sample of interest within the device,
(b) moving the said sample for dissolving the thermostable amplification constituents therein,
(c) mixing the sample and the thermostable constituents,
(d) applying a first temperature gradient in order to denature the nucleic acid of interest,
(e) moving the mixture for dissolving the non-thermostable amplification constituents therein,
(f) mixing mixture and non-thermostable constituents, and
(g) applying at least one second temperature gradient in order to amplify the denatured nucleic acid.

According to an embodiment, the thermostable amplification constituents of step (b) also contain restriction enzymes, which are not necessarily thermostable, but which allow the cleavage, into predetermined positions, of the nucleic acids of interest, which are deoxyribonucleic acids, prior to the application of the first temperature gradient of step (d).

According to another embodiment, which can be used in addition to the abovementioned embodiment, the detection of the amplicons consists, after step (g) in:

(h) moving the new mixture to dissolve the detection constituents therein,
(i) mixing mixture and detection constituents, and
(j) detecting the presence of amplicons.

According to another embodiment, which can be used in addition to at least one of the abovementioned embodiments, the amplification is a PCR amplification, for which the first temperature gradient is between 90 and 100° C., and the second temperature gradients are an alternation of the temperature in three different steps:

- between 90 and 100° C. for the first denaturation temperature, preferably about 94° C.,
- between 50 and 60° C. for the second hybridisation temperature, preferably about 55° C.,
- between 70 and 75° C. for the third polymerisation temperature, preferably about 72° C.

According to another embodiment, which can be used in addition to at least one of the abovementioned embodiments, the amplification is a post-transcriptional amplification (NASBA or TMA), for which the first temperature gradient is between 60 and 70° C., preferably about 65° C., and the second temperature gradient is between 40 and 50° C. for the second polymerisation temperature gradient.

According to another embodiment, which can be used in addition to at least one of the abovementioned embodiments, the first temperature gradient is applied to the first compartment and/or to the mixing means and the second temperature gradient(s) is/are applied to the mixing means and/or to the second compartment and/or to the third compartment.

According to another embodiment, which can be used in addition to at least one of the abovementioned embodiments, the first temperature gradient is applied for 5 to 20 minutes, preferably 15 minutes, and the second temperature gradient (s) is/are applied:

- in the case of a PCR amplification:
  - for the denaturation, for less than one minute, preferably from 2 to 20 seconds, preferably 5 seconds,
  - for the hybridisation, for less than one minute, preferably from 2 to 20 seconds, preferably 5 seconds, and
  - for the polymerisation, for less than two minutes, preferably from 5 to 80 seconds, preferably 10 seconds,
- in the case of a post-transcriptional amplification, for less than two hours, preferably from 5 to 80 minutes, and even more preferably:
  - about 60 minutes in the case of RNA target nucleic acids, or
  - about 90 minutes in the case of DNA target nucleic acids.

The following terms can be used equally in the singular or the plural.

The term “constituent” also means “reagent”, “amplification reagent”, “extraction reagent”, or “purification reagent” or “raw material” which designate reagents, such as reaction buffers, enzymes, mono-, bi- or triphosphate nucleosides, but also solvents, the salts required for carrying out a nucleic acid extraction, purification or enzymatic amplification reaction.

In the context of the present invention, “container” or “plastic container” means any receptacle such as tubes, pipette cones or tips, whether made from plastic (for example the Eppendorf type) or from glass or from all other materials.

In the context of the present invention, “nucleic acid” means a chain of at least two nucleotides, preferably at least ten nucleotides selected from the four types of nucleotides of the genetic code, that is to say, if the nucleic acid is a DNA:

dAMP (deoxyadenosine 5'-monophosphate),
dGMP (deoxyguanosine 5'-monophosphate),
dTMP (deoxythymidine 5'-monophosphate), and dCMP (deoxycytidine 5'-monophosphate), if the nucleic acid is an RNA:

AMP (adenosine 5'-monophosphate),

GMP (guanosine 5'-monophosphate),

UMP (uridine 5'-monophosphate), and

CMP (cytidine 5'-monophosphate).

The nucleic acid may also optionally comprise at least one inosine and/or at least one modified nucleotide. In the context of the present invention, the term "modified nucleotide" means a nucleotide, for example at least one nucleotide comprising a modified nucleic base, deoxyuridine, diamino-2,6-purine, bromo-5-deoxyuridine, or any other modified base, preferably with the exception of 5-methyl-cytosine. The nucleic acid may also be modified at the internucleotide bond, such as, for example, phosphorothioates, H-phosphonates, alkyl-phosphonates, in the structure such as, for example, alpha-oligonucleotides (FR-A-2.607.507) or polyamide nucleic acids (PMA) (Egholm M. et al.; J. Am. Chem. Soc.; 1992; 114; 1895-97) or 2'-O-alkyl-ribonucleotides and/or a 2'-O-fluoro nucleotide and/or 2'-amine nucleotide and/or an arabinose nucleotide, and LNA (Sun B. W. et al., Biochemistry; 2004; Apr. 13; 43; (14): 4160-69). Among the 2'-O-alkyl-ribonucleotides, the 2'-O-methyl-ribonucleotides are preferred, but use can also be made of 5-Propinyl Pyrimidine Oligonucleotides (Seitz O., Angewandte Chemie International Edition 1999; 38(23); December: 3466-69).

The term "nucleotide" defines either a ribonucleotide or a deoxyribonucleotide.

In the context of the present invention, "biological sample" or "liquid biological sample" means any sample that may contain nucleic acids. The latter may be extracted from tissues, blood, serum, saliva, circulating cells of a patient, or may originate from a food, an agrifood, or may even be of environmental origin. Extraction is carried out by any protocol known to a person skilled in the art, for example by the isolation method described in patent EP-B-0.369.063.

In the context of the present invention, "contaminant" or "contaminant acid" or "contaminant nucleic acid" or "contaminant element" means any nucleic acid whose amplification is not desired and which is liable to generate a false positive result during the detection.

"Amplification" or "amplification reaction" means any nucleic acid amplification technique well known to a person skilled in the art, such as:

PCR (Polymerase Chain Reaction), described in U.S. Pat. No. 4,683,195, U.S. Pat. No. 4,683,202 and U.S. Pat. No. 4,800,159, and its derivative RT-PCR (Reverse Transcription PCR), in particular in a one-step format, as described in patent EP-B-0.569.272. Preferably, the PCR is carried out on a single strand with a single primer pair.

LCR (Ligase Chain Reaction), described for example in patent application EP-B-0.201.184, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, TMA (Transcription Mediated Amplification) with U.S. Pat. No. 5,399,491, and RCA (Rolling Circle Amplification) described in U.S. Pat. No. 6,576,448.

In the context of the present invention, "target" or "target nucleic acid" or "nucleic target" or "target of interest" or "nucleic acid of interest" means a nucleic acid (an oligonucleotide, a polynucleotide, a fragment of nucleic acid, a ribosomic RNA, a messenger RNA, a transfer RNA) to be amplified and/or detected. The target may be extracted from a cell or chemically synthesised. The target may be free in solution or may be bonded to a solid support.

The term "liquid and biological sample of interest" means a homogeneous or heterogeneous aqueous solution.

"Solid support" means particles which may be made from latex, glass (CPG), silica, polystyrene, agarose, sepharose, nylon, etc. These materials may optionally allow the confinement of magnetic material. They may also be a filter, a film, a membrane or a strip. These materials are well known to a person skilled in the art.

The target may be a viral, bacterial, fungal nucleic acid, or yeast, present in a mixture, in the form of a single or double strand of DNA and/or of RNA. In general, the target has a length of between 50 and 10 000 nucleotides, but it is usually between 100 and 1000 nucleotides.

"Marker" means a molecule carried by a nucleotide. The link between the marker and the nucleotide can be made in various ways known to a person skilled in the art. Manual coupling is carried out by using markers carrying an activated group, typically a carboxyl or a thiol, which are coupled onto a modified internal nucleotide carrying the corresponding reagent group (amine or thiol, for example), or on one end of the modified nucleotide strand with these same reagent groups. Automatic coupling is obtained by using phosphoramidites carrying the marker, and the coupling is then carried out during the automated synthesis of the nucleotide strand, either on one end of the strand, or on an internal position, according to the type of phosphoramidite used. The marker may be a fluorophore or a fluorescence quencher.

"Fluorophore" means a molecule which emits a fluorescence signal when excited by light at a suitable wavelength. The fluorophore may in particular be a rhodamine or a derivative thereof such as Texas Red, a fluorescein or a derivative thereof (for example FAM), a fluorophore of the Alexa family such as Alexa 532 and Alexa 647, Alexa 405, Alexa 700, Alexa 680, Cy5 or any other fluorophore appropriate to the measuring instrument employed. Fluorophores available for detection probes are widely varied and known to a person skilled in the art.

In the context of the present invention, "fluorescein" means an aromatic chemical molecule which emits a fluorescence signal with an emission peak around 530 nm, when excited by light at a wavelength of about 490 to 500 nm, preferably 495 nm.

"Fluorescence quencher" or "quencher" means a molecule which interferes with the fluorescence emitted by a fluorophore. This quencher may be selected from non-fluorescent aromatic molecules, to avoid interfering emissions. Preferably, the said quencher is a Dabsyl or a Dabcyl or a Black Hole Quencher™ (BHQ) which are non-fluorescent aromatic molecules that prevent the emission of fluorescence when they are in the physical vicinity of a fluorophore. The fluorescence resonance energy transfer (FRET) technique can also be used as described for example in Fluorescent Energy Transfer Nucleic Acid Probes, p. 4, Ed. V. V. Didenko, Humana Press 2006, ISSN 1064-3745. The quencher may also be selected from fluorescent molecules, such as for example TAMRA (carboxytetramethylrhodamine).

The "three-base detection probe" or "three-base probe", called S3B, is a probe as defined previously and which, in addition to the preceding features, consists of a nucleotide chain of three different types of bases selected from the group of adenine, thymine, guanine, cytosine. It is well understood by a person skilled in the art that according to the form of the probes (Molecular Beacon, see EP95/904 104.7, EP96/303 544.9 and EP97/923 412.7, or O-probe, see PCT/FR2009/051315, etc.), the probe will consist of a portion of a sequence wherein the nucleotide chain comprises nucleotides of four different types of bases and a sequence wherein the nucleotide chain comprises nucleotides of three different types of bases (sequence allowing the hybridisation and detection of the amplicons).

In certain cases, to improve the hybridisation with the amplicons and hence their detection, the probes according to the invention may occasionally contain uracile instead of thymine. In this case, the probes according to the invention will consist of a nucleotide chain of four different types of bases (uracile, guanine, adenine, thymine).

"Hybridisation" means the process during which, under suitable conditions, two single-strand nucleotide fragments, having complementary sequences in whole or in part, are capable of forming a double strand or "duplex" stabilised by hydrogen bonds between the nucleic bases. The hybridisation conditions are determined by the stringency, that is to say, the rigour and the low salinity of the operating conditions. Hybridisation is increasingly specific when carried out at higher stringency. Stringency is defined in particular according to the composition in bases of a probe/target duplex, and also by the degree of mismatch between two nucleic acids. The stringency may also be a function of the reaction parameters, such as the concentration and type of ionic species present in the hybridisation solution, the type and concentration of denaturing agents and/or the hybridisation temperature. The stringency of the conditions under which a hybridisation reaction must be conducted will mainly depend on the hybridisation probes employed. All these data are well known and the appropriate conditions can be determined by a person skilled in the art.

The appended examples and figures represent particular embodiments and cannot be considered as limiting the scope of the present invention.

FIG. 1 shows a first embodiment of the inventive disposable device, which contains a single fluid channel. In this particular configuration, the device is ready to draw up a biological sample to be treated in which at least one target nucleic acid is likely to be present.

FIG. 2 also shows this first embodiment, but in another particular configuration, in which the device is in the course of drawing up the biological sample to be treated (not shown in this figure).

FIG. 3 shows a second embodiment of the inventive disposable device, which contains two fluid channels in parallel. In this particular configuration, the device is ready to draw up the said biological sample containing at least one target nucleic acid, likely to be present.

FIG. 4 also shows this second embodiment, but in another particular configuration, in which the device is in the course of drawing up the biological sample to be treated (not shown in this figure).

Figure 7:
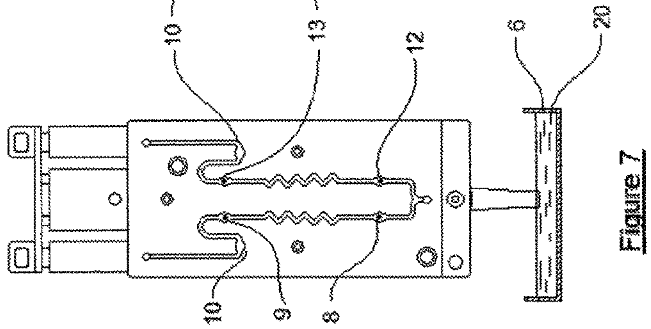

Finally, FIGS. 7 to 10 show the device according to an alternative of the second embodiment, but in the course of use:

FIG. 7: The disposable device does not contain the liquid sample of interest. Its tip is just in contact with the sample which is present in a container.

Figure 8:
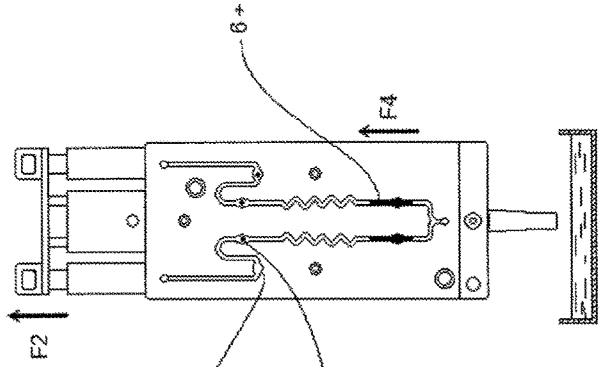

FIG. 8: The tip being in contact with the sample, the pistons are moved for drawing up the sample of interest into the disposable device. In this case, the sample is located in the first compartment and the thermostable constituents which it contains. Before the pistons have completed their drawing up in this phase, the disposable device is raised and/or the container is lowered, so that the device and sample of the said container are no longer in contact and the single channel is only filled with air, as is the case in this FIG. 8. The two downstream channels each contain a liquid column of an aliquot of the sample. Preferably, the drawing up by the pistons is stopped when the device is withdrawn from the sample remaining present in the container.

Figure 9:
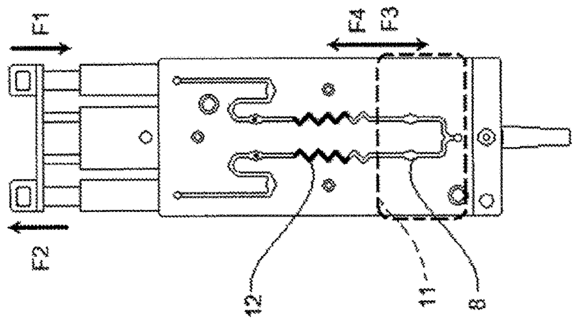

FIG. 9: The drawing up of the sample of interest by the said pistons continues and the said sample is transferred to the mixing means, where the back-and-forth motions allow the proper mixing of the sample and the thermostable constituents. The combination of the sample with the thermostable constituents will continue to be called "sample" for easier reading and understanding.

Figure 10:
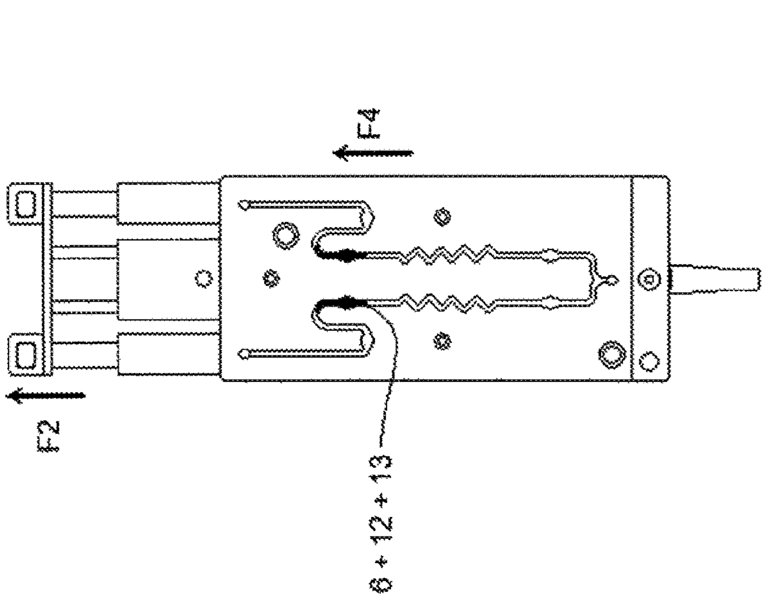

FIG. 10: The pistons are moved to allow the drawing up of the sample of interest into the disposable device. In this case, the sample is located in the second compartment and the non-thermostable constituents that it contains.

Figure 11:
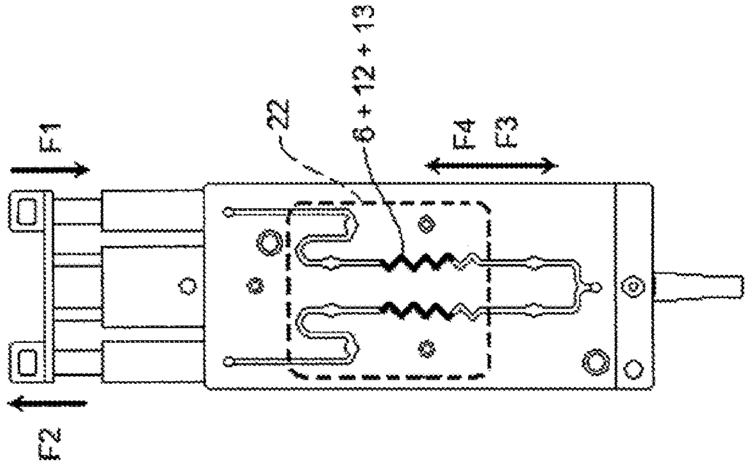

FIG. 11: The drawing up is suspended, but the sample of interest is discharged by the said pistons and the said sample is transferred to the mixing means, where the back-and-forth motions allow the proper mixing of the sample and the non-thermostable constituents. Once again, the combination of the sample with the thermostable and non-thermostable constituents will continue to be called "sample" for easier reading and understanding.

Figure 12:
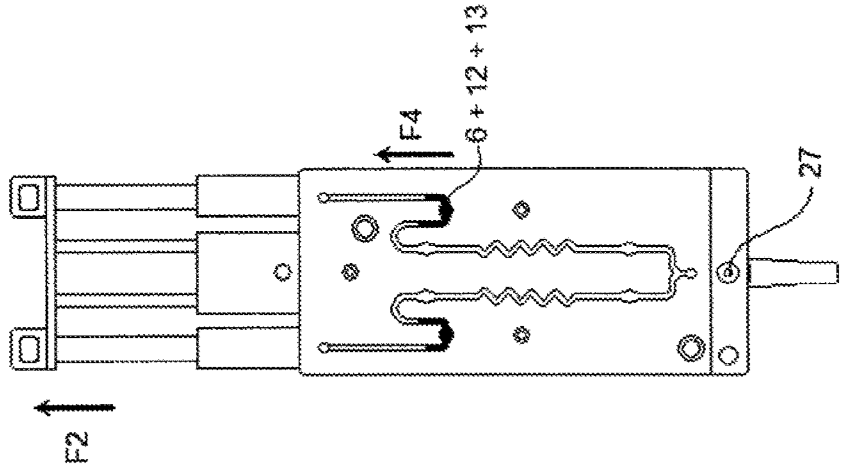

FIG. 12: The pistons are moved to allow the drawing up of the sample of interest into the disposable device. In this case, the sample is located in the third compartment and the constituents necessary for detection that it contains.

Figure 13:
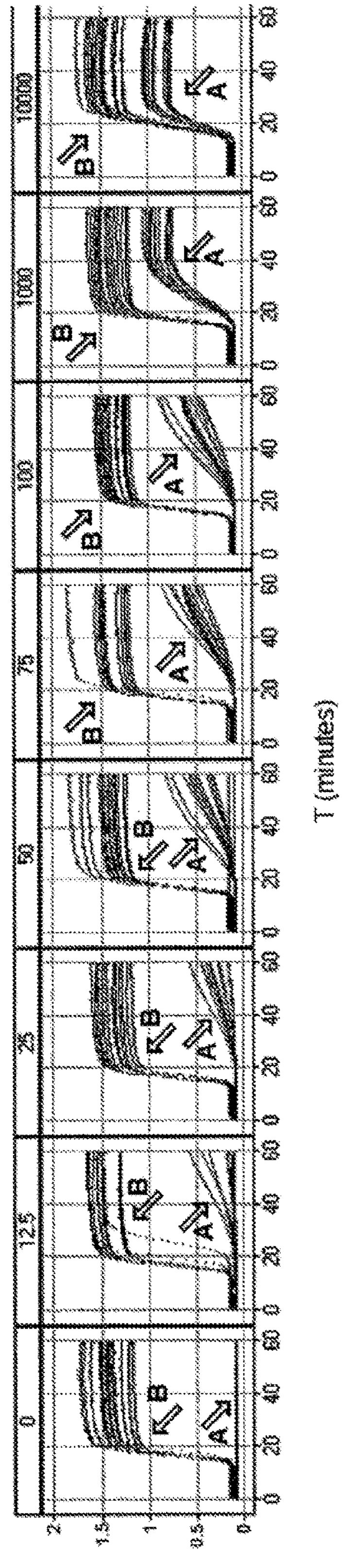

FIG. 13 shows NASBA amplification curves for the prior art (EasyQ) for increasing values of the quantity of target (see scale from 0 to 10 000 in the high position—see reference to the arrow B). The curves corresponding to the amplification of the HIV target sequence are plotted in the lower position (see reference to the arrow A), and the curves corresponding to the calibrator are in the upper position.

Figure 14:
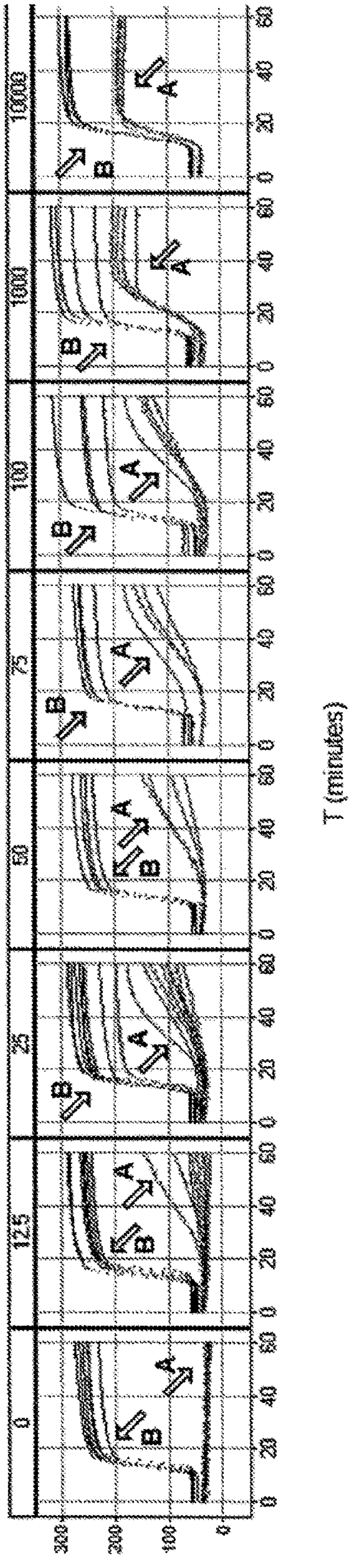

FIG. 14 shows the NASBA amplification curves for the invention under the same conditions as those applied in FIG. 13 (similarly for the use of the arrows A and B). It should be noted that to improve the legibility of this figure, the curves corresponding to the HIV target have been expanded by a factor of 5. Thus, with the device of the present invention, the curves corresponding to the target (HIV) vary from about 8 to 40 rfu (Relative Fluorescence Units). Since the curves of the calibrator vary from 50 to 250, the graph is not legible if the two curves are plotted with the same scale. As plotted, the HIV curves vary between 40 and 200 and are therefore more legible. Finally, these are relative values without prejudice to the effectiveness of the amplification, and it is actually the inflection points of each curve which have interpretative value.

Figure 15:
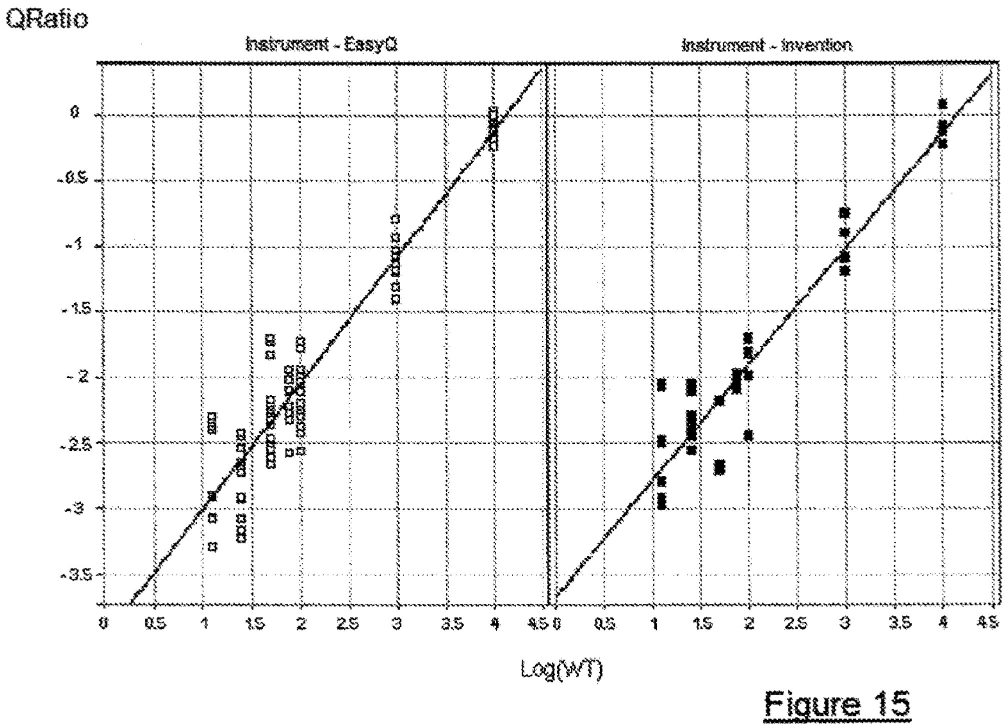

FIG. 15 proposes the variable quantification calculated by the algorithm HIV v. 2.0 for the EasyQ instruments (left) and according to the invention (right).

Figure 16:
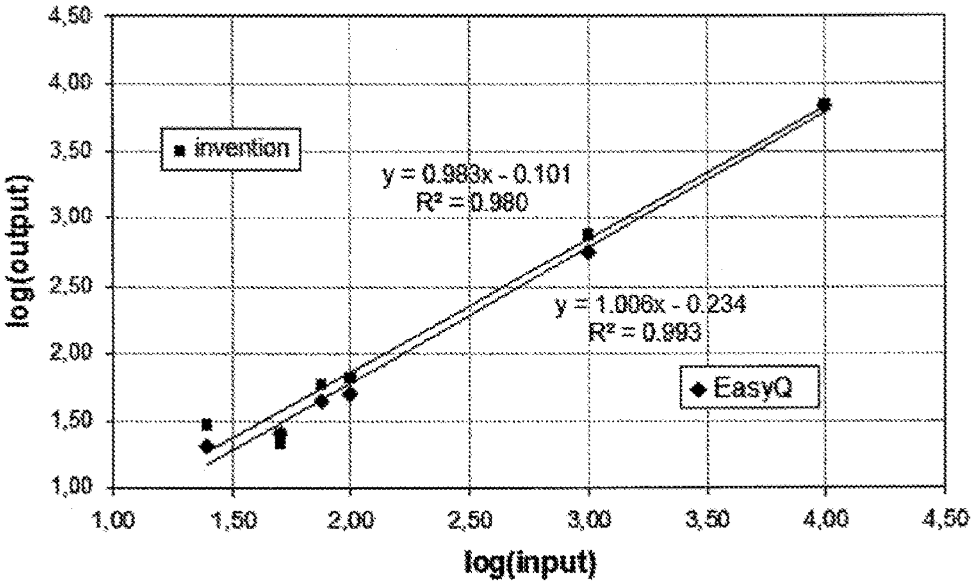

FIG. 16 shows the quantification result as a function of the quantity of target.

Figure 2:
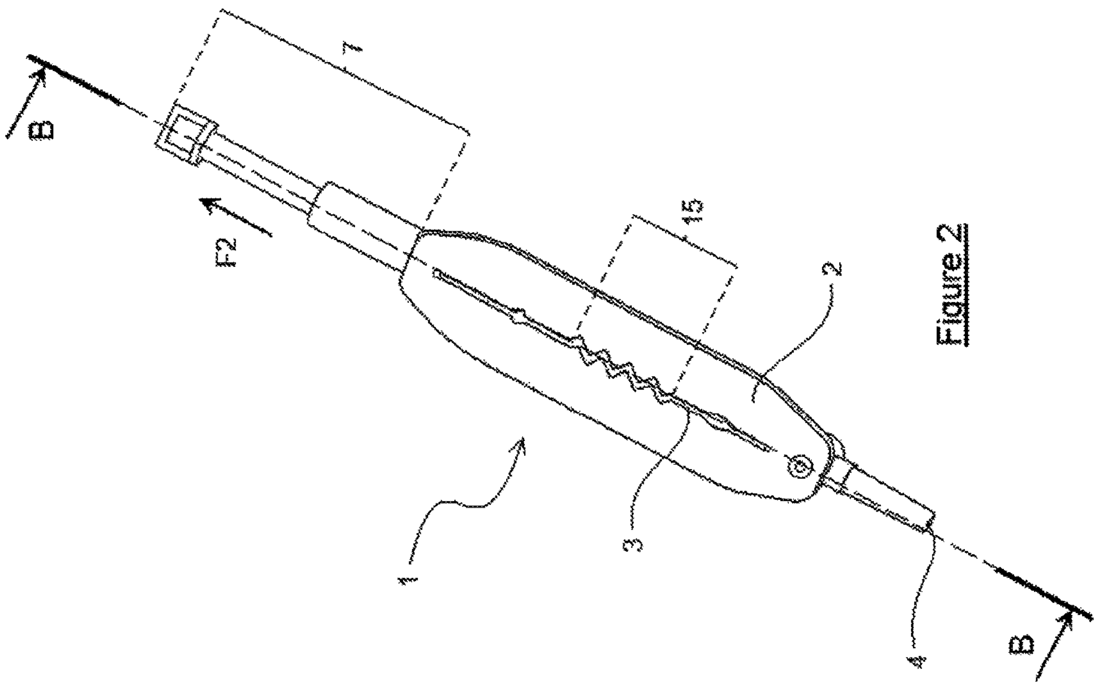
Figure 17:
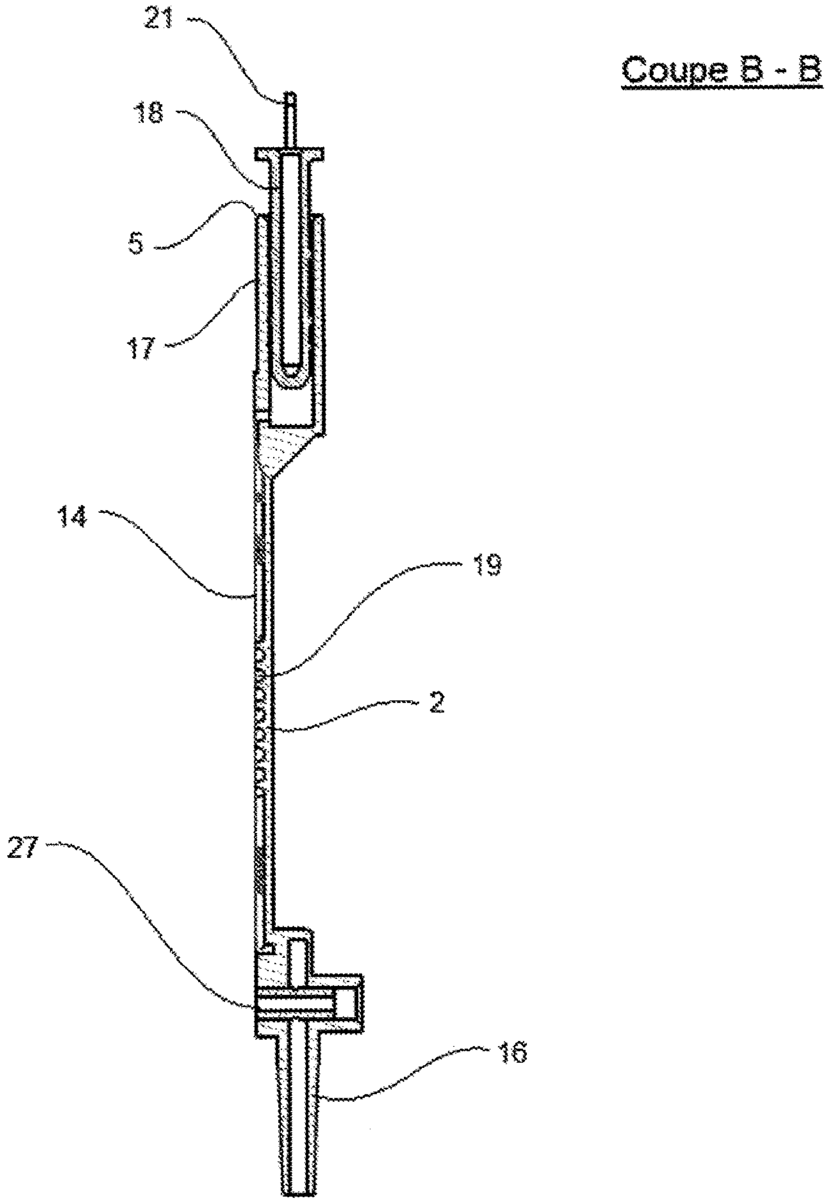

Finally, FIG. 17 shows a longitudinal section along B-B of FIG. 2 of the inventive device.

The present invention is clearly represented in the set of FIGS. 1 to 17. Three embodiments are shown more particularly.

Figure 1:
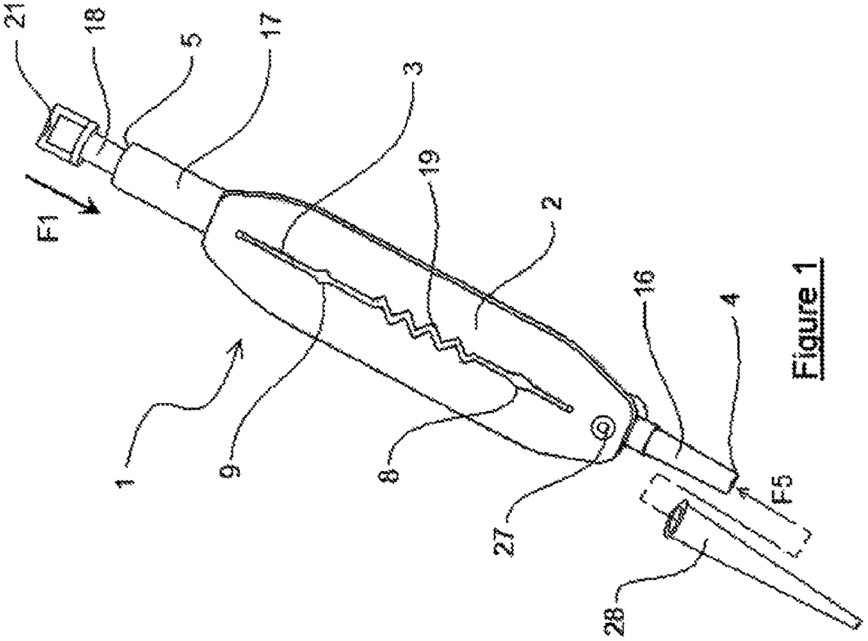

A first embodiment shown in FIGS. 1 and 2 represents a perfectly simple embodiment of the present invention. It consists of a disposable device formed of a solid body 2 in the surface of which a fluid circuit or channel 3 is etched. This fluid circuit 3 is obviously bounded by a film of the BOPP (Bi-Oriented PolyPropylene) type, not referenced in these two figures, but present with the reference 14 in FIG. 17, which prevents the liquid sample from leaving the said circuit 3. The fluid channel 3 comprises, on the one hand, a through hole 4, called inlet, at the bottom of each figure, and another through hole, called outlet, at the top of each figure, which enables the channel 3 to have two output openings. In fact, the inlet 4 is formed by a pipette tip, referenced 16, that is to say, moulded in a single part with the overall body 2. FIG. 1 shows an added on pipette tip 27, showing a particular embodiment using a conventional tip. On the other side, the outlet 5 is present in a cylinder 17, which constitutes one of the parts of the drawing up/discharging means 7. The other part of this drawing up/discharging means 7 consists of a piston 18 which can slide within the cylinder 17, moved by an actuator, not shown here, along the arrow F1, on the one hand, which is a movement of the piston 18 in the cylinder 19 in which the volume of fluid in the fluid circuit 3 decreases, or along arrow F2, which is a movement of the piston 18 in the cylinder 19 which is completely different from the previous one, that is to say, it increases the volume of fluid in the fluid circuit 3. The actuator can act on the piston via a linkage means 21. This system is particularly advantageous in the case in which the overall system is to be automated. In this embodiment in FIGS. 1 and 2, it should be observed that the fluid circuit is relatively simple because along the channel 3, having a substantially constant cross-section, it comprises a first compartment 8, a second compartment 9 and, between the compartments 8 and 9, a mixing means 15 consisting of a set of baffles 19. The roles of these compartments 8 and 9 and of this mixing means 15 are described more amply below.

Figure 4:
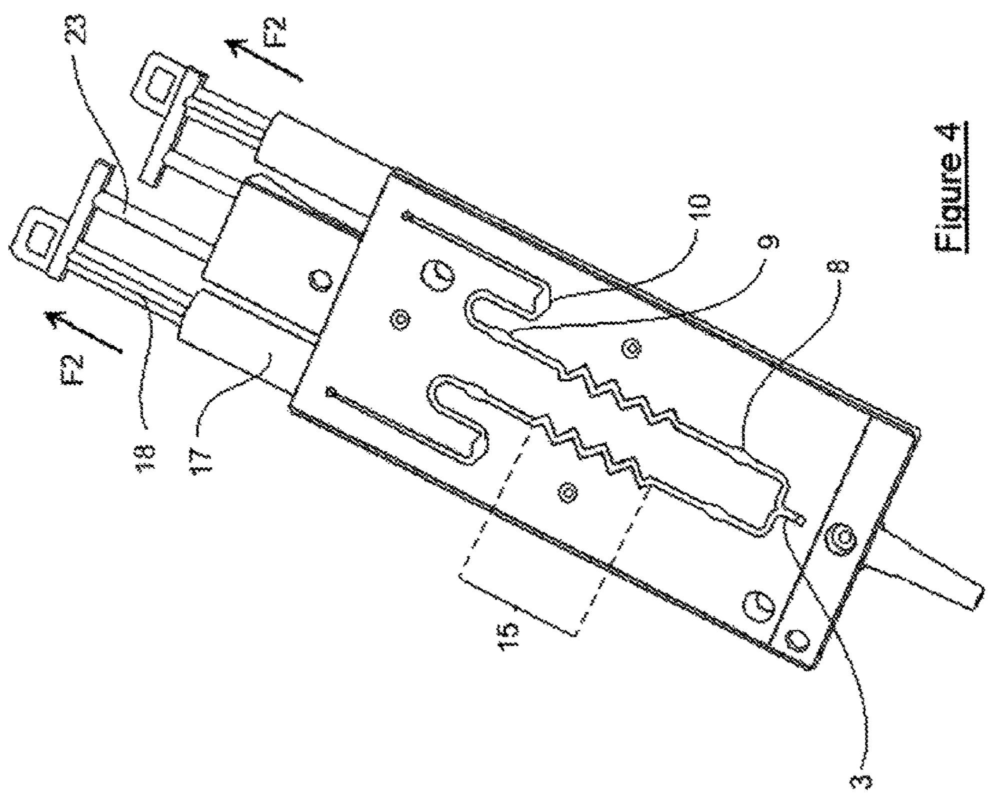
Figure 3:
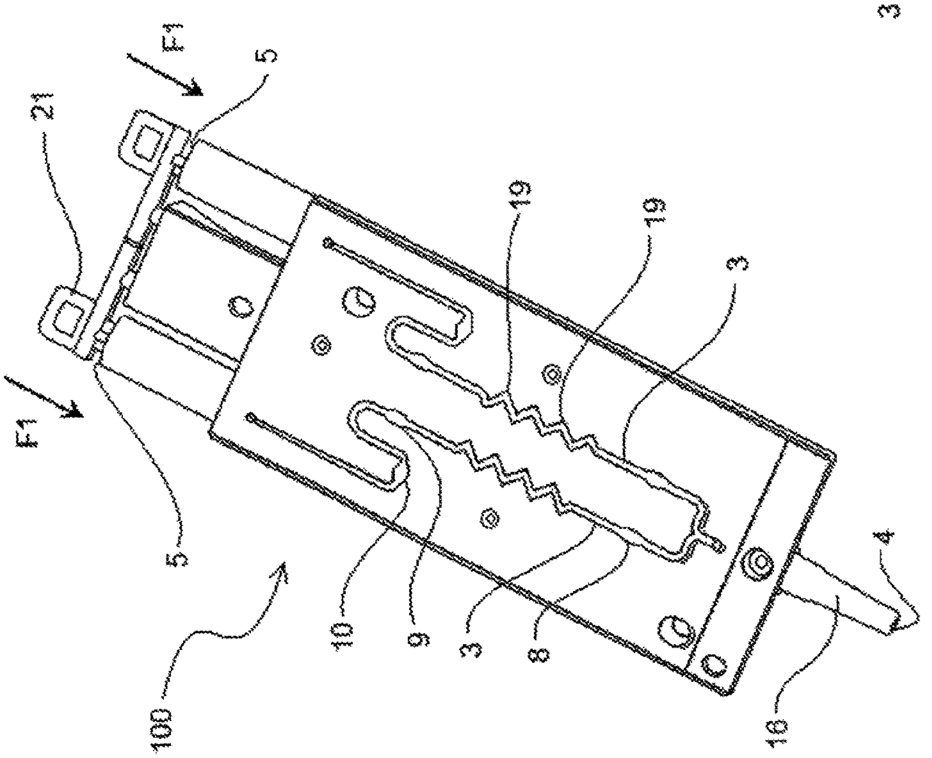

The second embodiment is shown in FIGS. 3 and 4. This is an embodiment that is substantially identical to the previous one, but in which two fluid channels are in parallel with one another. This device is referenced 100 although all the other elements have the same reference numerals as those previously used. FIG. 3 is substantially identical to FIG. 1 because the piston 18 is in the rest position, that is to say, it is in the low position in the cylinder 17, and the actuator or the manipulator moves the said piston 18 via the linkage means 21. In this embodiment, there is therefore an inlet 4, a single channel 3 on the downstream portion, which is then split into two channels of identical cross-section which rise in parallel along the body 2 of the device 100. Along each of the channels 3, as in the previous case, are located a first compartment 8, a mixing means 15 and a second compartment 9. However, there is also a third compartment 10 upstream. For practical reasons, a trap is formed between the second and third compartments 9 and 10, that is to say, the first bend of the trap is located above the first compartment 9 and the third compartment 10 is located at the second bend of the trap. Alternatively, the compartment 10 can be deleted and the reading made directly in the compartment 9. The role of the compartment 9 or 10 is primarily to secure any undesired movement of the liquid towards the lower part of the card, the said card being used in the vertical position, and then, to increase the volume of liquid usable for the fluorescence detection by maximising the diameter of the reading lid, made in the associated heating unit in the instrument, and to position it opposite the compartment 9 or 10. Another feature of this embodiment is that for an inlet 4, there are two outlets 5, because each channel 3 is connected upstream to a drawing up/discharging means 7. Hence each channel 3 is associated with a cylinder 17 and with a piston 18. In this particular embodiment, the two pistons 18 are independent of one another, as clearly shown in FIG. 4, that is to say, they can be actuated along F1 and F2 independently from one another.

The configuration with two individualised pistons, moving independently of one another, serves to correct the positioning defect of the liquid segments in each fluid channel individually, in particular by a recalibration of the said segments in the detection zone, for example, the shift possibly being due to an inhomogeneous viscous sample, a slight moulding defect in the fluid circuit of the card, or an undesired movement due to a thermal gradient momentarily creating a pressure differential on either side of the fluid segment. Hence this serves to increase the operating robustness of the device. This system operates whenever there is more than one channel, with the help of position sensors placed at appropriate locations, on the one hand, within the device, and on the other hand, with regard to the card according to the invention.

It should be noted that it is particularly advantageous to have an anti-extraction system for each piston 18. Thus, and advantageously, each piston 18 can be provided with a guide 23 that is connected by one end to the upper end of the piston rod 18 and at its other end, not shown in the figures, to a larger-section form preventing the accidental extraction of the post-amplification piston during handling by the operator (e.g. unloading of the consumable from the instrument at the end of analysis, or piston positioning error by the instrument). This anti-extraction system is obviously adaptable to all the embodiments considered by the present invention.

Figure 6:
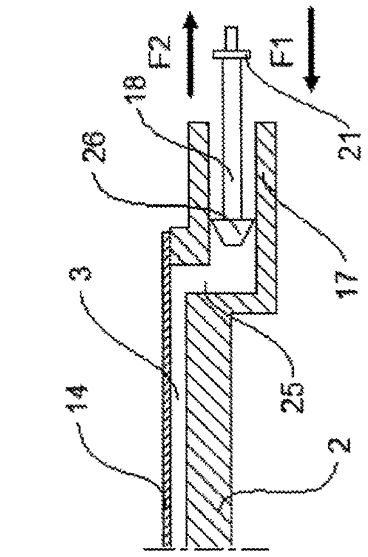
FIG. 6 shows a cross-section along A-A of FIG. 5 for better visualising the way in which the drawing up and discharging actions are conducted within the said device.
Figure 5:
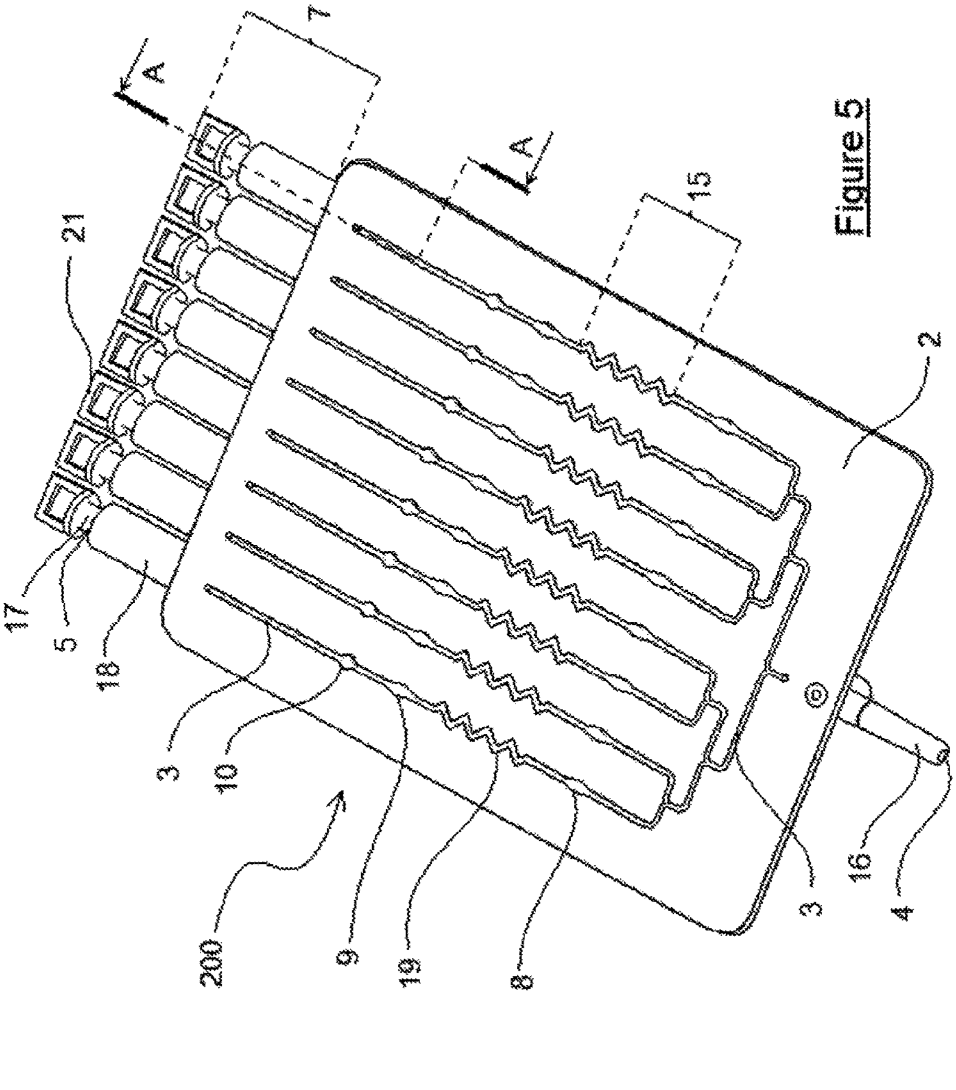
FIG. 5 shows a third embodiment of the inventive disposable device, which contains eight fluid channels in parallel. In this particular configuration, the device is ready to draw up the said biological sample containing at least one target nucleic acid, likely to be present.

FIGS. 5 and 6 show a third embodiment which is substantially identical to the previous one, except in that it comprises eight fluid channels 3 in parallel. As for the two preceding embodiments, there is only one inlet 4 located at a tip 16 from which a single channel leaves. This is divided into two to three repetitions, yielding a total number of eight channels 3 in the active portion of the device 200 and therefore eight outlets 5. Each channel 3 then consists of:

- a first compartment 8 followed by a mixing means 15 composed of a number of baffles 19,
- a second compartment 9, and finally
- a third compartment 10.

Each channel obviously terminates in a drawing up/discharging means 7 consisting, as usual, of a cylinder 17 and a piston 18. Similarly to the second embodiment, this third embodiment comprises pistons 18 which are handlable via the linkage means 21 in a self-contained and independent manner with regard to the other adjacent pistons 18.

FIG. 6 shows a longitudinal section along the axis A-A of FIG. 5, for better visualisation of the connection existing between the channel 3 and the drawing up/discharging means 7. This section serves to show the body 2 of the device 200, which comprises on its upper surface a channel 3 bounded externally by a partitioning film 14 made from an appropriate material. The film is preferably made from BOPP (Bi-oriented PolyPropylene) with a silicon cement, but may also be made from PP (PolyPropylene), PET (PolyEthylene Terephthalate), TPE (Thermoplastic Elastomer), or PP/PE type complex film which can be sealed by laser around the fluid channels. This channel 3 culminates in a transverse hole 25 which terminates in the cylinder 17. Present in this cylinder 17 is the piston 18, the piston head 26 of which forms a seal with the sleeve of the said cylinder 17. The piston head 26 may be composed of two parts (body with groove and elastomer O-ring) or may consist of a one-piece piston, simplifying the card assembly operations and serving to reduce the cost per test. It is therefore obvious that when the actuator or the manipulator applies a force along F2 on piston 18, the latter allows the drawing up of the gaseous or liquid fluid present in the channel 3, while the action along F1 serves to discharge this fluid via the outlet 4, not shown in FIG. 6.

Built-in pistons can be manufactured in two different ways. One is a simple piston with or without ring segment ("O-"), as in the above case, or a two-section piston. Although this type of piston is well known to a person skilled in the art, the use of a two-section piston has the following advantages:

- The intrinsic positioning accuracy is improved compared to a simple piston (having the same diameter) because the volume of liquid pumped is determined/calibrated by the difference in volume between the two sections of the said piston (the drawing up function is therefore located between the two diameters of this piston).
- After the pumping action, the piston is completely thrust into the sleeve/cartridge in which it is moved. This eliminates any risk that the piston will be extracted by user error.

FIGS. 7 to 14 show the second embodiment of FIGS. 3 and 4 during the use of the device 100. It should be noted that this device 100 is very slightly different from the one already described, because the two pistons in the present case are joined together so that the fluid motion in each of the two channels 3 is identical. This is obviously one alternative and the pistons can also be detached from one another, either automatically by the robot, or manually by the manipulator as required. It is also possible that the bridge connecting the two pistons can be deformed without necessarily being physically cut.

FIG. 7 shows that the liquid and biological sample 6 is exclusively contained in a container 20 although the latter 6 is in contact with the device 100; in particular, the tip 16 is partially immersed in the said liquid 6. The device 100 comprises, in addition to that which was shown in FIGS. 3 and 4, thermostable constituents 12 present in the first compartment 8 and non-thermostable constituents 13 in the second compartment 9. In fact, the constituents are stored in solid form, for example according to the technical data given in patent EP-B-0.641.389, which the reader is requested to consult for further details on this subject.

It is obviously conceivable for there to be only two compartments 8 and 9, as in FIGS. 1 and 2. In this case, it is necessary to have non-thermostable and detection constituents 13 and 14 which are present together in the second compartment 9. Similarly, if an amplification only having thermostable constituents is used, it is also possible to have all the ingredients present in a single compartment, 8 or 9 in particular. Preferably, the tip is matched to a pipetting cone 28, as shown in FIG. 1, for example with a capacity of 50 to 200 μL, or otherwise, which is not shown in the figures but is well known to a person skilled in the art, a polyethylene straw which can be thermally sealed after all the fluid sequences are produced in the card. In FIG. 7, either the container of the biological sample can rise in contact with the tip, or the card is brought by the instrument into contact with the liquid present in the container, the latter case corresponding to architectures for high-rate machines. The device will then be used as a conventional pipetting cone and will therefore be moved along the axes X, Y and/or Z by a robot to take a sample from the container or containers.

In FIG. 8, the linkage means 21 is moved along F2, so that the pistons 18 draw up the liquid sample present in the container 20 within the card. At the end of this step, not shown in this figure, the device 100 has been raised whereas the pistons 18 continue their drawing up action, explaining the presence of two liquid columns in each of the channels 3. It should be noted that the volume drawn up is related to the cross section of the piston built into the card and to the length of movement of the piston. Apart from the optional initial stop in the pipette cone, the first stop of each liquid sample 6 occurs in the first compartment 8, that is to say, at the thermostable constituents 12, thereby making it possible to dilute the said constituents which are actually stored in freeze-dried or dried form, as is the case for the other constituents 9 and 10. The liquid segment is kept on the reagent position to make it easier to place the dried or freeze-dried reagent in suspension again, typically for ten seconds, generally less than one minute.

In FIG. 9, the fluid continues to move along F4 towards the mixing means 15. This movement along F4 corresponds to the drawing up of the piston along F2. When the mixture 6+12 has reached the baffles 19, a back-and-forth movement along F3 and F4 is generated by a movement of the pistons along F1 and F2, to allow a more or less rapid passage, and on many occasions, of the said mixture within the mixing means 15. Typically, the number of mixture return trips in the card is between one and ten return trips, typically five return trips to guarantee a satisfactory homogenisation of the compounds of the reaction. The changes in direction due to the presence of the baffles thereby allow a good mixing of the dilute constituents, called thermostable constituents 12, within the liquid sample of interest 6. Thermostable constituents 12 means in particular the amplification primers, the detection probe or probes, the nucleotides and all other thermostable ingredients required to elongate the primers during the amplification.

FIG. 9 shows that a first zone exists intended for heating 11 shown by a dotted line. This zone symbolically represents the place where the manipulator or the robot applies a heat source in order to treat the liquid sample 6+12, that is to say, the sample 6 in the presence of the thermostable constituents 12, in order to begin an amplification technique such as NASBA.

When this is done, FIG. 10 shows that the drawing up along F2 continues, so that the liquid columns rise to the second compartment 9 or the non-thermostable constituents 13 are diluted in turn. This movement along F4 is always due to the rise of the pistons along F2. Non-thermostable constituents essentially means the enzymes required for amplification. In the context of a post-transcriptional amplification, in particular, this means AMV-RT (Avian Myeloblastosis Virus Reverse Transcriptase), RNase H and polymerase T7 (DNA dependent RNA polymerase).

For all the liquid movement steps, the flow rate is typically 1 μL per second. Advantageously, an optical sensor of the instrument, not shown in the figures, positioned about two millimeters before each reagent, loaded in the card, serves to detect the presence of the liquid segments and thereby to guarantee satisfactory operating robustness while compensating for the effects associated with the difference of each sample.

Alternatively, the use of optical sensors also makes it possible to measure the length of the liquid segment and therefore to check the accuracy of the liquid division made during the step of drawing up and loading the sample in the card.

In FIG. 11, each liquid column is then relowered along F1 to the level of the mixing means 15. At this level, the entire mixture 6+12+13 is also moved along F3 and F4, so that the baffles 19 allow a suitable mixing of the thermostable constituents 12 and non-thermostable constituents 13 within the sample 6. The arrival in the chambers can advantageously be detected by the fluorescence read head built into the instrument to make the real-time measurement of the amplification reaction.

FIG. 11, like FIG. 9, shows a second zone for heating 22 which also serves to carry out the NASBA amplification.

In FIG. 12, the drawing up along F2 enables the liquid columns 6+12+13 to rise to the third compartment 10, which accordingly acts as a read zone. It should be noted that this read zone may be the first compartment 8 or the second compartment 9 or the third compartment 10. In the present case, the third compartment 10 acts as a buffer zone to prevent any undesired rise of liquid towards the top of the device, and this action is reinforced by the closure of the valve 27.

If, however, the third compartment 10 acts as a read zone, the drawing up along F2 is greater, enabling the liquid columns 6+12+13 to rise to the said third compartment 10, where the reading can take place.

According to another embodiment, it is possible to provide for the thermostable constituents 12 to be split into two spheres, called pellets. A first sphere, present in the first compartment 8, contains the amplification primers, the nucleotides and any other thermostable ingredient required for the elongation of the primers during the amplification. A second sphere, present in the third compartment 10, contains the detection probe or probes required for detecting the amplicons, after the amplification step. In this case, the mixture must return to the level of the mixing means 15, within which the entire mixture is still moved along F3 and F4 so that the baffles 19 allow a suitable mixing of the thermostable constituents 12 and non-thermostable constituents 13 within the sample 6. The reading can take place in any one of the compartments 8, 9 or 10.

A final step exists, not shown in the figures, which consists, immediately after the end of the positioning in the third compartment, in closing the valve 27 by means of an actuator built into the instrument. Alternatively, the said valve can be deleted and replaced by a straw, as mentioned above, which can be sealed, for example by heat, and which then has two functions, that of pipetting the sample into the container, and then that of closure by the use of a heating wire within the associated instrument.

According to a particular embodiment, a small carousel can be associated with the device of the present invention. This carousel carries the various tubes required for carrying out an extraction step prior to conducting the method according to the said invention:

the first tube contains the biological sample to be treated, at least one second tube contains a washing buffer, a third tube for the elution buffer, and a fourth tube to recover the eluate.

The latter tube is optional, but useful for taking an aliquot, for example, to perform a sequencing before a new drawing up into the device for carrying out the amplification.

According to this novel embodiment, a silica filter is added either at the cone 16 or at the pipette cone 28. This silica filter is available from Akonni (Ref.: 300-10606, Frederick, Md., USA).

According to the method of use, the inventive device descends to draw up all or part of the biological sample to be tested (blood, urine, etc.) for about 5 to 100 μL in the first tube. These values are approximate because they are limited by the stroke and the volume of the piston (FIG. 1) or pistons (FIG. 3 for two pistons and FIG. 5 for eight pistons).

In case of a plurality of pistons, they move simultaneously to maximise the volume drawn up. Alternatively, the size (stroke and diameter) of the pistons built into the card can be increased in order to achieve the best compromise between drawing up a large volume of sample, on the one hand, and accuracy of movement of the eluate in the said device, on the other hand, during the amplification steps.

The sample is first lysed, optionally in the carousel in the presence of GuSCn or by ultrasound, in which case the tube is coupled with a sonotrode placed under the carousel. This sample is drawn up into the silica filter with, if necessary, return trips to increase its residence time in the filter and improve the nucleic acid (RNA/DNA) capture efficiency.

The remaining sample is then discarded in the first tube or in another receptacle or tube containing the waste.

The carousel then rotates to bring the second washing tube under the pipetting cone. The washing buffer is drawn up by the pistons, with mixing in the filter if necessary, and then discarded in the first tube or into another receptacle or tube containing the waste.

Optionally, the washing can be carried out at least once more. In this case, either the device draws up the same washing buffer as previously, if the latter has not already been used, or the carousel rotates to bring another second washing tube under the pipetting cone. The washing procedure is thus repeated with the washing buffer that is drawn up by the pistons, with mixing in the filter if necessary, and then discarded in the second tube or in the waste tube.

The carousel then rotates to bring the third tube containing the elution buffer under the pipetting cone. The tube plate may optionally be provided with a heating block in order to maintain the temperature of the elution buffer between the ambient temperature and 75° C., so as to improve the salting out of the nucleic acids from the filter if necessary.

A buffer volume of 10 to 160 μl (depending on the reaction volume per fluid circuit 3 and the number of circuits 3 per device) is drawn up by the pistons, with mixing in the filter if necessary, and then discarded either in the empty tube after rotation of the carousel (to recover the eluate) or directly transferred by drawing up into the card to start the amplification process.

EXAMPLE

This example shows the quantification performance obtained with a disposable device according to the second embodiment of the invention, that is to say, the card with two fluid channels in parallel (see FIGS. 3 and 4). The tests were performed using Human Immunodeficiency Virus (HIV) as target.

Our invention was compared with a product already marketed, called Nuclisens EasyQ analyzer (Ref. 285060, bioMérieux S.A., Marcy l'Etoile, France), using the same biological samples, containing synthetic HIV targets.

1—Preparation of Targets

The transcripts were introduced into the two apparatus: Nuclisens EasyQ and according to the invention. There was no sample preparation step, like extraction, for example.

2—Materials and Methods

The experiments on EasyQ were performed using the bioMérieux HIV2.0 kit (hereinafter called PVB1) (Ref. 285033, bioMérieux B.V., Boxtel, Netherlands), following the instructions for use. The kit contained:

- a mixture of enzymes: a sphere of enzymes, hereinafter called ENZ (batch No.: 83281SXX)+45 μL enzyme diluent (83301AXX), and
- a mixture of primers and probes hereinafter called P/B: there are in fact two P/B spheres (batch No: 83283SXX), to which 180 μL of diluent were added for P/B 2× (83272AXX).

This gave a NASBA mixture with 5 μl of mixture ENZ and 20 μl of mixture P/B+15 μL of targets.

The inventive disposable device is completely automated for the amplification and detection. It makes it possible to take the biological sample to be tested, containing the targets.

The experimental protocol of the inventive device is defined for the reagents (primers, probes and enzymes in particular) to have the same concentration as in the EasyQ protocol. However, the volume per test used in our invention is 5 μl instead of 40 μl as with EasyQ. The quantity of reagents is therefore divided by eight. The reagents from the PVB1 kit were freeze-dried and placed in the inventive device. The freeze-drying bench is associated with a Hamilton pipettor robot (Ref. 202997, Bonaduz, Switzerland) which allows the reproducible deposition of droplets of 1 μL for P/B and 1.25 μL for ENZ in the dedicated compartments of the inventive device.

The amplification and detection instrument used with the invention performs all the functions required to obtain an amplification curve, that is to say, the drawing up of the sample, mixing the reagents, heating and fluorescence reading. This concept eliminates most of the mandatory manual steps with EasyQ.

Table 1 below shows the main differences between EasyQ and the invention.

TABLE 1

Comparison of technical data and of the method used by the prior art device (EasyQ) and by the invention

| | EasyQ | Invention |
|---|---|---|
| Volume | 40 μL | 5 μL |
| P/B | 20 μL | 1 μL (incorporated) |
| ENZ | 5 μL | 1.25 μL (incorporated) |
| Volume of sample used | 15 μL | 5 μL |
| Manual Steps | dilute the accuspheres, Add primers and probes to the eluate transfer to the incubator, add the enzyme solution to the plug, close the tube with the plug, centrifuge, run on the vortex, centrifuge again, load the tube in the analyzer and start. | Load the tube in the analyzer and start |
| Number of tests/series | Up to 48 tests | 2 with the device proposed |

As stated above, the biological sample used for this study contained HIV targets. This sample was then diluted for the experiments on EasyQ and the invention, but the same series of dilutions were used. Table 2 below shows the number of HIV targets per test and the number of experiments performed with each of the two devices (EasyQ and invention). The number of pre-extraction “equivalent” copies corresponds to the number of copies needed upstream of an extraction step to obtain the number of copies per test (i.e. pre-extraction “equivalent” is equal to the number of copies per test divided by the extraction yield).

TABLE 2

Number of HIV targets per test and number of experiments performed with each of the two devices (EasyQ and invention)

| | | | | | | | | |
|---|---|---|---|---|---|---|---|---|
| Number of copies of target per test (EasyQ and invention) | 0 | 3.75 | 7.5 | 15 | 22.5 | 30 | 300 | 3000 |
| Number of copies of pre-extraction “equivalent” per test | 0 | 12.5 | 25 | 50 | 75 | 100 | 1000 | 10 000 |
| Number of replicates with EasyQ | 15 | 12 | 12 | 15 | 12 | 15 | 15 | 15 |
| Number of replicates with the invention | 8 | 8 | 8 | 4 | 4 | 4 | 4 | 4 |

“Replicate” means the number of times that the test was performed in parallel using the same initial sample. The number of copies for internal inspection was 290 per test, both for EasyQ and for the invention.

Note that in the present case, the invention does not allow two tests in parallel, so that the number of replicates is considerably lower with our invention than with EasyQ.

The detection limit claimed for EasyQ is 25 copies (pre-extraction equivalent), corresponding to 7.5 copies per test.

The data acquired with EasyQ were processed with the EasyQ Director software (BioMérieux S.A., La Balme, France), using the HIV-1 DB 2.0 test protocol (Ref. 285033, bioMérieux B.V., Boxtel, Netherlands). Each amplification curve, measured with the instrument using the invention, was processed by using an internal tool like EDrecalc recalculation concerning the algorithm for computation and interpretation of the amplification curves, which is included in the EasyQ Director commercial software mentioned above, with the same algorithm as the one used by the EasyQ Director software and the HIV-1 DB 2.0 test protocol.

3—Results

The raw fluorescence curves are shown in FIG. 13 for the prior art device (EasyQ) and in FIG. 14 for the invention. The amplification curves obtained with the invention are very similar to those obtained with EasyQ. A broad distribution of fluorescence values can be observed for the fluorescence plateau of the signal from the calibrator. Since this distribution exists with each instrument, this propagation is not associated with the instrumentation.

3.1—Detection Limit:

Owing to the small number of replicates, it is not possible to determine the detection limit with a narrow confidence interval. Thus, in Table 3 below, we have only compared the number of positive results obtained with the two instruments for a few values of the number of copies extracted from Table 2:

TABLE 3

Detection limit with each of the two devices (EasyQ and invention)

| | Input values (pre-extraction "equivalent" copies per test) | | | | |
|---|---|---|---|---|---|
| | 0 | 12.5 | 25 | 50 | 75 |
| Easy Q Number of positives/number of experiments | 0/15 | 6/12 | 12/12 | 14/15 | 12/12 |
| Invention Number of positives/number of experiments | 0/8 | 5/8 | 8/8 | 4/4 | 4/4 |

The detection limit claimed for the NucliSENS HIV 2.0 test is 25 copies (detection limit at 95% positives). With this input value, all the tests performed with the inventive device were positive. With 12.5 copies, about 50% of the tests were positive with EasyQ and slightly more with the invention. It can therefore legitimately be considered that our invention has results at least similar to the detection limit of the prior art, EasyQ.

3.2—Quantification Performance:

FIG. 15 shows the Qratio (quantification variable) as a function of the number of input copies. The distribution of the points corresponding to the data is similar for both instruments.

Using the parameters associated with the reagent batch, a person skilled in the art can obtain the number of copies by calculation, and the mean thereof is plotted on a logarithmic scale in FIG. 16.

Tables 4 and 5 below show the qualification performance associated with these two instruments:

TABLE 4

Qualification Performance for EasyQ

| Input Data | Log (Input) | Mean | Accuracy | Degree of Accuracy |
|---|---|---|---|---|
| 25 | 1.40 | 1.31 | 0.19 | 0.09 |
| 50 | 1.70 | 1.40 | 0.20 | 0.30 |
| 75 | 1.88 | 1.64 | 0.19 | 0.24 |
| 100 | 2.00 | 1.70 | 0.23 | 0.30 |
| 1000 | 3.00 | 2.75 | 0.14 | 0.25 |
| 10 000 | 4.00 | 3.83 | 0.07 | 0.17 |

TABLE 5

Qualification Performance for the Invention

| Input Data | Log (Input) | Mean | Accuracy | Degree of Accuracy |
|---|---|---|---|---|
| 25 | 1.40 | 1.47 | 0.18 | 0.07 |
| 50 | 1.70 | 1.34 | 0.33 | 0.36 |
| 75 | 1.88 | 1.77 | 0.05 | 0.11 |
| 100 | 2.00 | 1.82 | 0.34 | 0.18 |
| 1000 | 3.00 | 2.89 | 0.21 | 0.11 |
| 10 000 | 4.00 | 3.84 | 0.13 | 0.16 |

According to the high level specifications of the HIV2.0 test, the accuracy, that is to say, the standard deviation of the results of the various replicates, must be lower than 0.3 log. Some accuracy values for the data of the instrument prototype associated with the device are above this specification. This may be due to the small number of replicates, which preclude a correct estimation of the accuracy.

The prototype clearly meets the specification for the degree of accuracy (that is to say, the difference between the result and the number of test input copies) is 0.25.

The linearity for the invention is the same as for EasyQ, but needs to be measured above the $10^4$ copies of this study.

4—Conclusion

The present invention, in its configuration with two parallel fluid channels, was used to detect HIV targets by means of the HIV v. 2.0 kit. The results were compared with the EasyQ analyser, which served as a reference.

The performance of the invention was in line with the most severe constraints required for performing an HIV test (HIV v. 2.0) and are at least comparable to those recorded with the EasyQ analyser.

Since the invention used a reaction volume of 5 μL (instead of 40 μL for EasyQ), the quantity of the reagents per test was divided by eight. This gives rise to a much lower production cost per test, because this cost is mainly due to the enzymes, accounting for about 80% of all the ingredients in the kit. The inventive device also significantly reduces the number of manual steps, because only three basic actions are required to launch a test:

Loading of the inventive device;

Loading the tube containing the extracted targets (by the EasyMAG extraction apparatus (Ref. 200111, bioMérieux SA, Marcy l'Etoile, France)), and Starting the test.

REFERENCE NUMERALS

1—Disposable device
2—Solid body of the device 1
3—Fluid circuit or channel in the body 2
4—Through hole of channel called inlet
5—Through hole of channel called outlet
6—Liquid and biological sample of interest
7—Drawing up/discharging means
8—First compartment along channel 3
9—Second compartment along channel 3
10—Third compartment along channel 3
11—First zone intended for heating
12—Thermostable constituents present in compartment 8
13—Non-thermostable constituents present in compartment 9
14—Boundary film
15—Mixing means

16—Built-in pipette cone or spindle accommodating a cone 28
17—Cylinder of the drawing up/discharging means 7
18—Piston of the drawing up/discharging means 7
19—Baffle of the mixing means 15
20—Container in which the sample 6 is initially present
21—Means of linkage with an actuator
22—Second zone intended for heating
23—Guide of piston 18
25—Through hole
26—Piston head
27—Final closure or sealing valve
28—Conventional pipette cone
100—Disposable device with two parallel channels 3
200—Disposable device with eight parallel channels 3
F1—Movement of piston 18 in cylinder 19 which decreases the volume of fluid in fluid circuit 3
F2—Movement of the piston 18 in the cylinder 19 which increases the volume of fluid in fluid circuit 3
F3—Movement of the sample 6 under the action of movement F1
F4—Movement of the sample 6 under the action of movement F2
F5—Socketing of cone 28 on sleeve 16

The invention claimed is:

1. A disposable device for amplifying at least one target nucleic acid present in a liquid and biological sample of interest, which comprises:

a solid body containing at least one fluid channel connecting an inlet comprising a tip, wherein the inlet accommodates a cone of a pipette that is added on to the tip or wherein the tip of the inlet has a pipette-cone-shaped configuration, via which all or part of the sample of interest can be drawn up and/or discharged, and an outlet opening connected to a device for the drawing up and/or discharging of the said sample of interest, the fluid channel further comprising from the inlet to the outlet opening:

a slide valve which can be closed, a first compartment containing all or part of thermostable constituents required for producing the amplification, a means for mixing the thermostable constituents, optionally combined with non-thermostable constituents, with the sample of interest, wherein the mixing means consists of the fluid channel, the routing of which comprises at least one baffle, a second compartment containing all or part of the non-thermostable constituents required for producing the amplification, and in addition, at least one zone intended for heating the said sample of interest mixed with the said thermostable and non-thermostable amplification constituents, in order to allow the amplification of the target nucleic acid, the device for the drawing up and/or discharging of the sample of interest comprising a cylinder connected to the fluid channel and a piston moving within the cylinder to draw up said sample from the first compartment to the mixing means, mix, then draw up to the second compartment, then relower to the mixing means for mixing.

2. The device according to claim 1 further comprising, in the second compartment, all or part of the detection constituents required for detecting amplicons.

3. The device according to claim 1 further comprising, in the fluid channel, a third compartment containing all or part of the constituents required for detecting amplicons.

4. The device according to claim 3, wherein the third compartment is located between the second compartment and the outlet opening of the device.

5. The device according to claim 1, wherein the drawing up and/or discharging device further comprises a pipette.

6. The device according to claim 1, wherein the cross-section of the channel is constant and that the first and second compartments have a larger cross-section.

7. The device according to claim 1, wherein the inlet communicates with at least two fluid channels.

8. The device according to claim 1, wherein the outlet opening comprises at least two fluid channels.

9. The device according to claim 1, wherein the constituents are formed of freeze-dried or dried biological compounds, soluble in the sample of interest.

10. The device according to claim 1, wherein the drawing up and/or discharging device is an integral part of the disposable device.

11. The device according to claim 10, wherein the piston moves within the cylinder-manually or moves within the cylinder by means of an actuator.

* * * * *